United States Patent [19]

John

[11] 4,193,964
[45] Mar. 18, 1980

[54] MICROMINIATURE PALLADIUM OXIDE GAS DETECTOR AND METHOD OF MAKING SAME

[75] Inventor: Frank T. John, Williamsville, N.Y.

[73] Assignee: A-T-O Inc., Willoughby, Ohio

[21] Appl. No.: 862,974

[22] Filed: Dec. 21, 1977

[51] Int. Cl.² .................. G01N 27/04; H01C 3/00
[52] U.S. Cl. ................... 422/90; 23/232 E; 422/97; 338/34
[58] Field of Search .............. 23/232 E; 422/88, 90, 422/95, 96, 97, 119; 338/34

[56] References Cited

U.S. PATENT DOCUMENTS

| | | | |
|---|---|---|---|
| 2,904,406 | 9/1959 | Moore | 23/232 E |
| 3,092,799 | 6/1963 | Baker | 422/95 |
| 3,607,084 | 9/1971 | Mackey | 23/232 E |
| 3,625,756 | 12/1971 | Taguchi | 422/88 |
| 3,644,795 | 2/1972 | Taguchi | 422/119 |
| 4,063,898 | 12/1977 | Fisher | 23/232 E |
| 4,111,658 | 9/1978 | Firth et al. | 23/232 E |

Primary Examiner—R. E. Serwin
Attorney, Agent, or Firm—Christel, Bean & Linihan

[57] ABSTRACT

A microminiature palladium oxide gas detector and its method of manufacture. The detector comprises an extremely small coil of extremely fine wire such as platinum which is retained, sealed and insulated with an amorphous ceramic binder. The detector further comprises a catalyst applied to its exterior surface. The detector is manufactured by winding the wire about a mandrel which is desirably molybdenum. The coil is then coated with the binder composition which preferably comprises reduced chromic and phosphoric acids. The binder is then cured to retain the coil and the mandrel is removed by etching or oxidation. The catalyst is then applied which is preferably palladium nitrate in a weakly acidic hydrolyzed solution which has been adjusted to a pH of about 3 with tertiary octyl amine. The catalyst is then dehydrated and calcined desirably using an automatic electronic pulse controlled machine to precisely adjust and control processing temperatures and times. When hydrolyzed palladium oxide is used as the catalyst, the processing temperature never reaches the point where the oxide becomes reduced to the metal.

46 Claims, 4 Drawing Figures

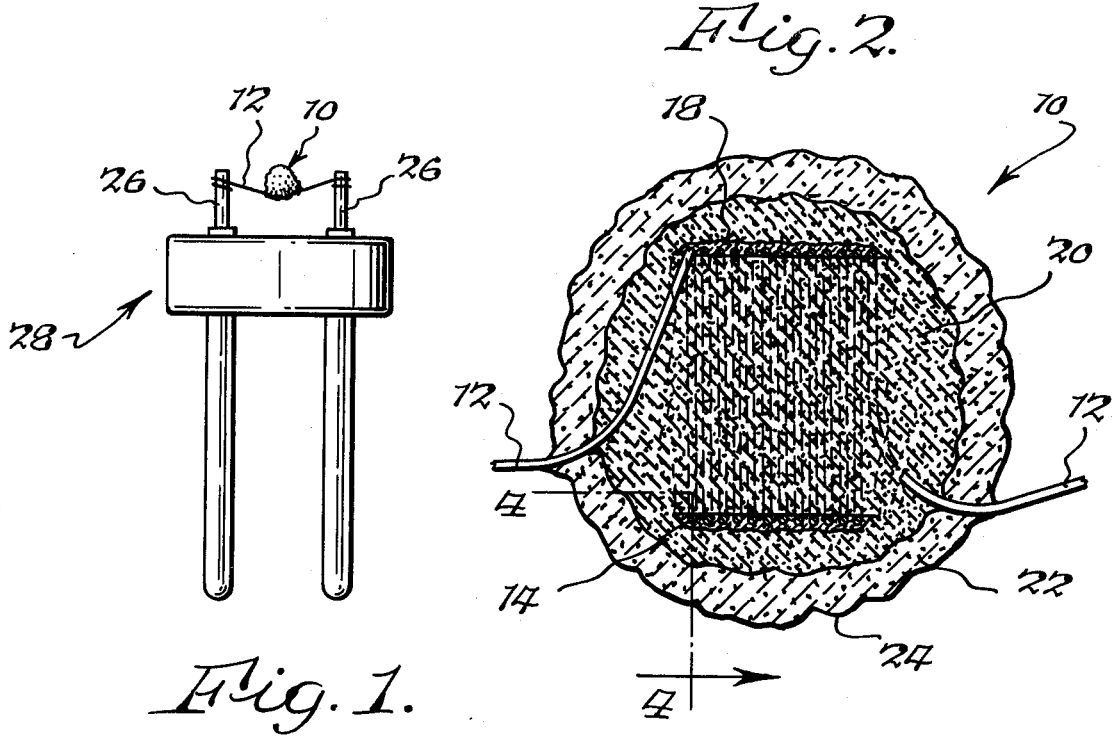
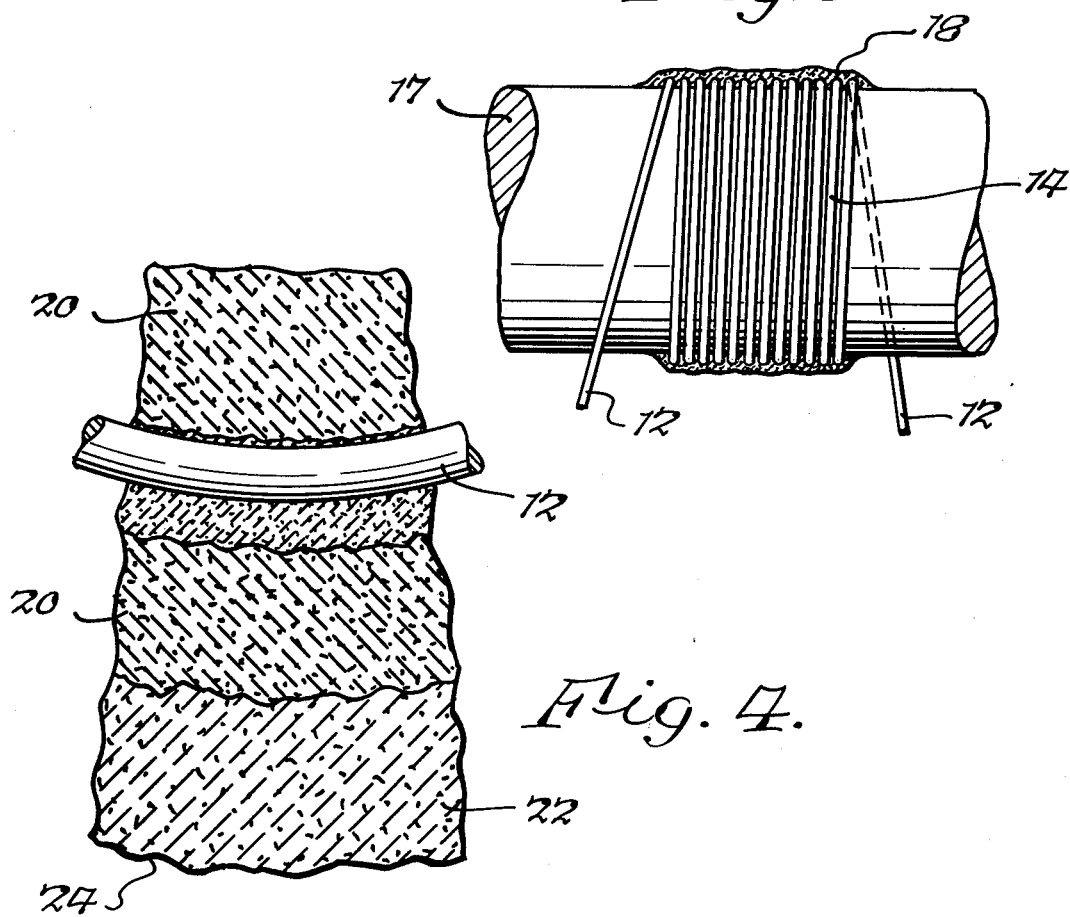

MICROMINIATURE PALLADIUM OXIDE GAS DETECTOR AND METHOD OF MAKING SAME

BACKGROUND OF THE INVENTION (a) Field of the Invention

This invention relates to detectors or sensors for determining the presence of a combustible gas in air and more particularly relates to detectors which detect a change in temperature when a combustible gas is oxidized at the surface of the detector.

(b) History of the Prior Art

In the prior art, gas detectors are known which comprise a metal wire which is connected as a resistance into a wheatstone bridge circuit and is electrically heated to a temperature of about 900° C. At that temperature a combustible gas will oxidize at the surface of the wire, further increasing the temperature of the wire, which in turn alters the electrical resistance of the wire which is detected by the wheatstone bridge circuit. Such detectors are unsatisfactory for many reasons. The wire must be manufactured from a high melting metal such as palladium or platinum which has catalytic properties. Even when such exotic metals are used, palladium or platinum metal vaporizes from the surface of the wire at the high operating temperatures, thus causing early failure of the metal wire detector. Additionally, even slight vaporization results in a change in the resistance of the wire, thus necessitating frequent zero adjustments to the bridge circuit.

Such detectors additionally are insufficiently sensitive for many applications since they are usually unable to detect the presence of a combustible gas at concentrations lower than about 300 ppm. Furthermore, the large size and high operating temperatures of such detectors utilize an undesirably high amount of electrical energy. These detectors also had undesirably long response times and were frequently position sensitive.

A few of the disadvantages of the wire type combustible gas detector were overcome when it was recognized that the wire could be wound in a coil and coated with a ceramic material containing a compound such as palladium chloride or chloroplatinic acid ($H_2PtCl_6 \cdot 6H_2O$) which would convert to a catalytic metal upon application of sufficient heat. Alternatively, a catalytic metal could be condensed upon the ceramic coating by heating a catalytic metal in close proximity to the coating.

Such detectors are disclosed in U.S. Pat. Nos. 3,092,799 and 3,200,011 to A. R. Baker; 3,564,474 to Firth et al and 2,816,863 to Page.

While such detectors were an improvement over the wire type detectors by preventing vaporization of the wire by means of the ceramic or refractory coating material, such detectors continued to have the disadvantage of vaporization of the catalytic metal at the surface of the detector, thus substantially reducing sensitivity. Additionally such detector sometimes continued to have varying responses depending upon the orientation of the detector. In order to maintain at least some sensitivity, such detectors were dependent upon diffusion of additional catalytic metals through the ceramic material to the surface. Such detectors therefore continued to have characteristics which varied over their useful life and continued to have poor sensitivity. The prior art detectors were relatively large and in order to maintain their catalytic surfaces at usuable temperature, much energy was dissipated through conduction, convection, and radiation. Additionally the operating temperatures, although slightly lower than the operating temperatures frequently utilized with a wire detector, continued to be undesirably high, thus substantially reducing the useful life of the detector and utilizing undesirably high quantities of electrical energy.

Such energy requirements were not only wasteful but also required large batteries in portable instruments.

Of particular importance is the fact that prior art sensors lack zero stability in the absence of combustible gas and failed to stay in calibration when subjected to prolonged exposure to the low levels of combustible gas frequently present in industrial environments. These effects are due to the fact that although some prior art sensors used palladium oxide, the oxide was only a thin veneer on palladium metal.

When viewed under a microscope, prior art sensors have a blue-to-violet iridescent black appearance characteristic of thin oxide films on palladium metal. Some patches on the sensor frequently show gray metal. By contrast, the sensor of the present invention varies in appearance from prior art sensors since iridescence and gray metal are not visible.

Furthermore, such sensors could not be made sufficiently small since the most suitable metals could not be wound in sufficiently small coils. It is known that the lamp industry uses proprietary machines to wind very small coils of tungsten wire on mandrels; however, these machines are unable to wind such coils from metals such as platinum or palladium since the coils do not retain their shape.

BRIEF DESCRIPTION OF THE INVENTION

There is provided in accordance with this invention a detector for combustible gases in air which has high sensitivity, i.e., is able to detect combustible gases in concentrations as low as 1 to 10 ppm. The detector in accordance with the present invention is substantially smaller than prior art detectors and requires a comparatively low operating temperature which in turn reduces the amount of electrical energy utilized by the detector and increases the useful life of the detector. Furthermore, the detector in accordance with this invention, after an initial break-in period, has a more uniform, i.e., less variable, sensitivity over its useful life.

Rather than using a catalytic metal, a detector of the present invention utilizes palladium oxide or palladium oxide hydrate ($PdO \cdot nH_2O$) as the catalyst. The new hydrate catalyst increases the sensitivity of the detector while at the same time permits lower operating temperatures. Additionally, the detector in accordance with the present invention utilizes a wire having a smaller diameter than the wires utilized in prior art combustible gas detectors. The use of the smaller wire accomplishes several purposes. One purpose is to increase the sensitivity of the detector since it requires less heat to alter the resistance of the thinner wire. Another purpose is to reduce the quantity of electrical energy needed to heat the wire to its operating temperature. The thin wire further permits the use of a smaller quantity of protective ceramic material which reduces the amount of heat required to raise the temperature of the ceramic material surrounding the wire. Such reduction in the quantity of heat required to raise the temperature of the ceramic material decreases energy requirements of the sensor while at the same time reduces the amount of combustible gas which must be oxidized in order to increase the temperature of the sensor to produce a usable signal.

The detector in accordance with the invention is an element which, at a temperature of below about 600° C., undergoes a change in electrical resistance when exposed to a combustible gas in air. The element comprises a wire coated with a palladium nitrate or ammonium chloropalladite solution which is heated to from about 100° C. to about 600° C. to form a palladium oxide composition. The preferred solution is a palladium nitrate solution which is most preferably hydrolyzed in a weakly acid solution and heated to from about 100° C. to about 600° C, preferably 500° C. to 600° C., to precipitate and to calcine palladium oxide hydrate. The wire comprises a metal or metal alloy having a melting temperature above 1500° C. and desirably has a circular cross section having a diameter of from about 0.0001 cm to about 0.0025 cm. Desirably, a coating of ceramic materials is present between the wire and the palladium oxide hydrate.

The invention further comprises a method for the manufacture of the element which comprises winding the wire around a mandrel having a diameter of from about 0.01 to about 0.1 cm to form a wire coil, the mandrel being more susceptible to oxidation than the wire. After the oil is formed, it is coated with a ceramic precursor solution.

The ceramic precursor solution preferably contains phosphoric acid and chromic acid anhydride reduced by aluminum trihydrate, aluminum hydroxide or hydroxides of other metals. To the solution is added 5 to 10% tabular alumina, or other full sintered high temperature oxide, having a particle size of less than 0.5 micron. The proportions of the ingredients of the precursor solution should, on a dry basis, desirably have the molar ratios of about $Al_2O_3:0.8Cr_2O_3:3P_2O_5$. Cerama-Bind, manufactured by Aremco Products Inc., is a commercially available mixture containg aluminum phosphate and phosphoric acid which has been found suitable for blending with a water insoluble metal oxide such as $Al_2O_3$. The coil is then heated slowly to above about 255° C. to remove water of crystalization and to dehydrate the coating. The coating is cured by raising the temperature to between 500° C. to 600° C. to form a cured ceramic binder coating having a thickness of from about 0.001 cm to about 0.025 cm. The mandrel is then removed by chemical or thermal oxidation.

The coil is then coated with a uniform solution containing from about 1 to about 50, preferably from about 2 to about 10 weight percent of palladium nitrate, $Pd(NO_3)_2.4H_2O$, or ammonium chloropalladite and the coil is heated to a temperature of from about 250° C. to about 750° C. for from about 1 to about 60 seconds to convert the palladium solution to a palladium oxide composition.

In accordance with the method of the invention, prior to coating the coil with palladium nitrate solution, the coil is desirably coated with a solution of from about 5 to about 60 weight percent, preferably 35 to 55% of aluminum nitrate, $Al(NO_3)_3.9H_2O$, and heated to convert the aluminum nitrate to aluminum oxide. The solutions can be as dilute as desired at the expense of applying additional coats. Permitting the solutions to stand at least 4, preferably 24, hours before use is desirable. Solutions should be discarded after about one month.

The small size of the sensor, the high surface area of the catalyst support and good catalyst dispersion result in a sensor having improved speed of response and sensitivity and which is not position sensitive.

BRIEF DESCRIPTION OF THE DRAWINGS

FIG. 1 is a side elevational view of a detector connected to electrodes at about ten times actual detector size.

FIG. 2 is an enlarged cross sectional side view of a sensor manufactured in accordance with the invention.

FIG. 3 is an enlarged cross sectional view of a wire coil wound upon a mandrel.

FIG. 4 is an enlarged sectional view as seen in the direction of the arrow shown in FIG. 2.

DETAILED DESCRIPTION OF THE INVENTION

"Combustible gas", as used herein means a gas, a vapor, or an atmospheric dispersion of fine particles which will react chemically at or near the surface of the detector and thereby change the detector temperature, when it is operated below about 600° C. Examples of such gases or vapors are carbon monoxide; methanol; ethanol; isopropanol; formaldehyde; ethylene oxide; terpenes; aliphatic hydrocarbons such as methane, ethane, propane, isobutylene, and octane; and cyclic hydrocarbons such as benzene, toluene, xylene, and nitrobenzene.

"Sensitivity" as used herein means the degree of ability to provide a meaningful signal which is distinguishable from background noise.

Comparative sensitivity measurements between detectors are made either by comparing the ratios of the changes in resistance from the air resistance, or by comparing millivolt bridge signal output for a specified input such as 2.5 volume percent $CH_4$ in air.

"Cure" or "curing" as used herein means heating to a sufficient temperature to render a substance water insoluble and self-adherent at elevated temperatures such as above about 800° C. The curing temperature in the case of phosphate and chromate containing ceramic precursor solutions is usually between about 440° C. and about 600° C.

In accordance with the invention, there is provided an element; i.e., a detection device, for detecting the presence of a combustible gas in air. The combustible gas is usually the gas or vapor of a carbon containing compound but may also be other combustible gases such as hydrogen.

The element in accordance with the invention may detect particular combustible gases at temperatures well below 600° C. For example, methane is detected at a temperature of between about 365° and 600° C., hydrogen is detected at a temperature as low as about 50° C., usually below 250° C., and carbon monoxide is detected at a temperature of about 280° C.

The detector element 10 in accordance with the invention, as seen in FIG. 1 and FIG. 2, is a wire 12 coated with a palladium compound. Microminiature sensors of this invention can be made using chloride compounds such as $PdCl_2$, $H_2PdCl_4$, $(NH_4)_2PdCl_4$, etc. but require special aging or other treatments to remove the chlorine, which is a known catalyst poison. At least two methods may be used. One consists of prolonged heating, i.e., (days) at elevated temperatures, e.g., from about 200° C. to about 650° C. which are well below those at which the oxide is destroyed. The other method is to fuse the chloride compound with an alkaline metal carbonate to precipitate the chlorine so that later the chloride salt can be leached out by boiling water.

Preferably the detector is coated with hydrolyzed palladium nitrate solution. The coated element for any of the compounds is then heated to from about 100° C. to about 350° C. to convert the palladium compound such as palladium nitrate to a palladium oxide composition which is desirably palladium oxide hydrate. Most of the impurities such as chlorine which can affect catalyst dispersion are removed at this temperature. Next, the detector temperature is raised preferably to from 500° C. to 600° C. for further curing and stabilising. If chlorine or hydrogen is present and the low temperature step is omitted, the catalyst particle size is increased by agglomeration and the detector sensitivity is reduced. Palladium nitrate is preferably hydrolyzed in a weakly acidic solution prior to application so that the desired palladium oxide hydrate is obtained upon heating. Palladium nitrate complexes such as tetramine palladous nitrate $[(NH_3)_4Pd](NO_3)_2$ may also be used.

The wire 12 is preferably a metal or metal alloy, having a melting temperature above 1500° C. and having a high temperature coefficient of resistance. Examples of usuable metals for the wire are platinum, palladium, nickel, rhodium, ruthinium, iridium, vanadium, zirconium and their alloys. Particularly desirable metals for use in the wire of the element are platinum and palladium due to their high resistance to oxidation. A particularly desirable wire is manufactured from platinum or a platinum alloy such as an alloy of about 90 weight percent platinum and about 10 weight percent rhodium. Platinum is particularly desirable because of its high temperature coefficient of resistance. Alloys of platinum and rhodium are desirable due to high strength.

The wire 12 of the element 10 is of a small diameter, preferably between about 0.0001 and about 0.005 cm and most preferably between about 0.0008 and 0.002 cm. The small wire diameter permits more rapid heating of the wire when heat of combustion of the gas is detected at the palladium oxide surface of the element. The use of a small wire permits a very small detector, i.e., from about 0.005 to about 0.2 cm in diameter, to be manufactured.

The wire 12 may be turned or bent into any desirable shape and is preferably in the form of a coil 14, as seen in FIGS. 2 and 3, to permit the use of a long wire in a given volume. The coil diameter is between about 0.002 and about 0.1 cm. For ease of manufacture, the coil diameter is preferably at least about 0.01 cm. The wire 12 may have any desirable cross section such as triangular, hexagonal, round, rectangular or square.

When the wire 12 is a coil 14 in accordance with the preferred embodiment, it is usually formed by winding the wire around a mandrel 17 preferably having a diameter of from about 0.01 to about 0.1 cm to form the wire coil 14. In order to form such a small coil, precision winding is necessary.

It is desirable to have the turns of the coil close to the surface of the detector to optimize sensitivity and to maximize the length of the wire within the volume of the detector within the limits of wire strength. A large ratio of coil diameter to wire diameter is therefore desirable to maximize the wire length. Prior art methods used in winding lamp coils or mandrels to retain coil shape cannot be used since lamp coils use a small ratio of coil diameter to wire diameter which permits the shape of such coils to be retained by the stiffness of the wire. The mandrel 17 is manufactured from a material such as molybdenum which is more susceptible to oxidation than the wire.

After the coil 14 is wound, it is desirably coated with a ceramic binder precursor solution. Any suitable ceramic binder may be used. "Ceramic binder" as used herein includes high temperature inorganic contiguous compositions whether of crystalline or amorphous character. "Ceramic precursor" is a solution or dispersion which will form a ceramic binder upon heating to above about 250° C. The resulting binder should be waterproof, be corrosion resistant, be electrically insulating, be able to fill the spaces between the turns of the coil prior to curing, and have sufficient strength to retain the shape of the coil and the spacing between turns. The ceramic precursor should cure to the desired binder at a temperature well below 900° C. to minimize changes in wire resistance due to vaporization of a portion of the metal wire. The binder should have good surface area and other characteristics known to those skilled in the art, if the binder is used as the catalyst support. Otherwise, if a catalyst support is applied over the binder, the binder should provide a good ceramic adhesive surface with high thermal conductivity. Of primary importance is the thermal stability of the binder, as well as freedom from sintering following preliminary heat treatment and aging. The size, thermal conductivity, and radiation characteristics preferably are constant or at least changing only very slowly (weeks), to permit stable detector performance and freedom from long-term noise which would otherwise require frequent recalibration of the instrument.

Although numerous silicon-based binders and high temperature glasses can be used, for long-term stability it is preferable not to use binders involving a silicon compound in combination with the very small diameter support wires of this invention. Many researchers have found that in a reducing atmosphere in the presence of trace quantities of carbon, iron, or sulfur, minute quantities of silicon metal migrate to wires such as platinum causing lowering of the melting point, embrittlement, and changes in resistance. These adverse results become increasingly important as the wire size is reduced to make very small detectors. See Thermocouple Temperature Measurement by P. A. Kinzie, pages 27, 34, 64, 73, and 174, published by John Wiley & Sons, 1973 and the references contained therein.

It is further desirable that the binder adhere to the wire of the coil to prevent shorting between turns and to provide good thermal conductivity. The binders should be free of lumps or agglomerates which cannot penetrate and remain between the desirably very closely spaced turns of the coil.

The binder should be unaffected by corrosion which might otherwise result from atmospheres frequently found in detector applications. In addition, the binder must be free of any catalyst poisons. The viscosity of the binder precursor should preferably be between 20 and 80 centipoise to permit application to the coil wound on the mandrel, as, for example, by a fine camel hair brush. Many prior art binder compositions are unsuitable for use in accordance with this invention. A binder which does, however, meet these and other desirable criteria for detector use is an inorganic polymer consisting of complex phosphate compounds of metals and metal oxides such as aluminum, chromium, zirconium, magnesium, zinc, calcium, barium, tin, titanium, thorium, and other metals which form acid-proof oxides.

A particularly preferred binder composition is prepared by heating 85% $H_3PO_4$, AlOOH, 60% $H_2CrO_4$, and $H_2O$ together at 100° C. to 130° C. for approximately one hour with slow mixing and constant stirring. Any lumps and particles are removed by straining. The resulting mixture contains aluminum and chromic acid phosphates in water solution. The mixture is allowed to stand overnight and 5 to 10 weight percent of a metal oxide powder such as alpha $Al_2O_3$ powder is added. The alumina is preferably fully sintered at a high temperature, e.g., tabular alumina, and ground to a particle size of less than 0.5 micron, Water is then added to bring the binder to a viscosity of preferably about 50 centipoise for convenience of application.

The amounts of the ingredients used should approximate in the dry state the formula molar ratios of: $Al_2O_3:3P_2O_5$ to $Al_2O_3:0.8Cr_2O_3:3P_2O_5$ where the molar ratio of $Cr_2O_3$ to $Al_2O_3$ varies from 0 to 0.8.

When phosphoric acid ($P_2O_5$) and aluminum oxide ($Al_2O_3$) are used alone, various ceramic precursor formulation in molar ratios and the characteristics of the resulting binders are given below:

| | |
|---|---|
| $P_2O_5/Al_2O_3 = 2.3$ | Precipitates solids, hardens on standing, makes poor bonds |
| $P_2O_5/Al_2O_3 = 3$ | Metastable |
| $P_2O_5/Al_2O_3 = 3$ to 3.5 | Maximum bond strength and usable solution stability |
| $P_2O_5/Al_2O_3 = 1.4$ | Usable solution but weak bonds because of excess $H_3PO_4$ |

The best molar ratio is seen to be $Al_2O_3:3P_2O_5$. The appropriate molar ration for other ceramic precursor systems can similarly be readily determined by one skilled in the art.

The binder containing chromic acid ($Cr_2O_3$) is superior in binding strength and thermal stability and is usable for for several months before clouding begins to appear, at which time it should be discarded.

The starting binder is best made using water dispersible aluminum trihydrate, $Al(OH)_3$ or aluminum monohydrate, AlOOH, such as Dispal (Philadelphia Quartz Company) or Baymal (Dupont), and slowly adding this mixture to heated 85% phosphoric acid. The phosphoric acid, $H_2CrO_4$, is made by adding chromic oxide, $CrO_3$, to water. The $CrO_3$ may be mixed directly or as a 50 to 60 weight percent water solution. The chromium is hexavalent and should be partially reduced to the trivalent form for best adhesion and long term binder characteristics. Reduction of the chromium to trivalent form can be accomplished by reducing with hydroxides of the metals chosen for the binder, or, if metals or oxides of metals are used, by reducing with inorganic hydroxides, or hydrogen peroxide. Preferably, the chromium is reduced by by using a low molecular weight organic amine, such as 3-amino-1-propanol, trithenolamine, or other alkanolamine or an amine in combination with a carboxylic acid sequestering agent to preserve the solution, such as oxalic acid, citric acid, gluconic acid, sulfosalicylic acid, tartaric acid. Other sequestering agents such as acetyl acetone may also be used. The latter combination enables the ceramic precursor to stand for months without clouding or deteriorating. Sequestering agents to preserve the solution, such as carboxylic acids, may be used alone without an amine at a 1:1 ratio with the 85% $H_3PO_4$ in the ceramic precursor.

When the binder alone is used as the catalyst support, it has been found useful to make the binder from ammonium phosphate, $NH_4H_2PO_4$ and metal nitrates, such as $Al(NO_3)_3.9H_2O$ and $Cr(NO_3)_3.9H_2O$, in a molar ratio of $NH_4H_2PO_4$ to metal nitrate of from 1.5:1 to 1.75:1. An amine is desirably used to adjust the pH. The resulting binder when dried and heated to 500° C. to 600° C. has a very large surface area and is particularly suitable as a catalyst support.

After the coil 14 is coated with the ceramic precursor solution, it is heated slowly up to a temperature of above about 250° C., then rapidly up to about 500° C. to about 600° C. to dehydrate and to cure the coating. The temperature preferably should not exceed 600° C. The resulting binder coating 18 is desirably from about 0.0002 to about 0.004 cm thick. The resulting ceramic coating retains the shape of the coil after the mandrel is removed. Other suitable ceramic precursor solutions such as colloidal silica may be used to treat the coil to form a ceramic coil-retaining coating. Such coatings should be compatible with the wire, thermally stable, and should contain no catalyst poisons.

After the aluminum phosphate coating is dehydrated and cured, the mandrel 17 is removed by chemical or thermal oxidation.

A suitable metal for use as a mandrel 17 is molybdenum since it can be removed by dissolving it in an aqueous solution containing from about 15 to about 40 parts by weight sulfuric acid, from about 15 to about 40 parts by weight nitric acid, and from about 30 to about 70 parts by weight water. Alternatively, a molybdenum mandrel can be removed by heating the mandrel in air at a temperature of between about 750° C. and about 1000° C. Many other metals can be used as the material for the mandrel 17. Examples of other metals which can be removed by chemical etching are aluminum, zinc, and iron. Molybdenum is particularly desirable since essentially no residue remains upon the coil 14 after the mandrel 17 is oxidized. In the preferred embodiment of the invention, the mandrel 17 comprises a molybdenum cylinder.

After the mandrel is removed, the coil 14 retains its shape due to the aluminum phosphate coating 18 which becomes water insoluble, even to boiling water, and essentially gas impervious after dehydration and cure. The preferred binder is amorphous over a wide temperature range and does not undergo changes which would permit the passage of gases, vapors or liquids through the binder.

After the mandrel is removed by chemical or thermal oxidation, the coil 14 is preferably coated with an aqueous solution containing from about 2 to about 10 and most preferably from about 4 to about 7 weight percent of hydrolyzed palladium nitrate or with an aqueous solution containing from about 2 to about 10 weight percent of ammonium chloropalladite. And then the coil 14 is heated to a temperature of from about 250° C. to about 500° C. for from about 1 to about 60 seconds to form a surface comprising palladium oxide hydrate or palladium oxide. The solution is preferably a palladium nitrate solution and the surface preferably comprises palladium oxide hydrate. Whenever coating with a palladium nitrate solution is subsequently mentioned herein, it is to be understood that a coating with an ammonium chloropalladite or alkali chloropalladite solution can be substituted with somewhat reduced detector sensitivity. The palladium nitrate is desirably hydrolyzed in a weakly acid solution, i.e., pH 2 to 4.

Desirably, prior to coating the coils 14 with a solution of palladium nitrate, the coil 14 is coated with a solution containing from about 5 to about 60, preferably from about 35 to about 55, weight percent of aluminum nitrate and heated to a temperature of between about 250° C. and about 750° C. to convert the aluminum nitrate to aluminum oxide. The resulting aluminum oxide coating 20 is preferably from about 0.001 to about 0.025 cm thick.

The resulting aluminum oxide coating 20 further protects the wire from vaporization and oxidation. If desired, more than one coating of aluminum nitrate can be applied over the coil for additional protection and strength.

Desirably and preferably, subsequent to coating the wire with aluminum nitrate solution and prior to coating with palladium nitrate solution, the coil is coated with a solution containing from 5 to about 70, preferably from about 40 to about 65, weight percent of thorium nitrate and heated to between 250° C. and 750° C. to convert the thorium nitrate to thorium oxide. The resulting thorium oxide coating 22 provides a ceramic surface having a large surface area upon which the palladium nitrate solution can be applied. The resulting high surface area increases the sensitivity of the element 10. The thorium oxide coating 22 is preferably from about 0.001 to about 0.025 cm thick.

Repeated applications and conversions of thorium solution can be made after application and conversion of aluminum nitrate and before application of palladium nitrate. Most desirably at least two coats of thorium nitrate solution are applied to the element 10 and up to about 10 repeated applications may be desirable for certain applications. Similarly, as previously discussed, repeated applications and conversions of aluminum nitrate solution can be made prior to application of the thorium nitrate or palladium nitrate solutions. Preferably at least two to four coats of aluminum nitrate solution are made prior to application of thorium nitrate and up to about 10 repeated applications and conversions of aluminum nitrate solution are desirable.

Multiple applications of palladium nitrate solution are desirably made upon the thorium oxide surface. The solution is most preferably a 0.27 molar hydrolyzed palladium nitrate solution. Desirably at least 15 coats of palladium nitrate solution are made and up to about 20 such applications continue to improve the sensitivity of the element. After the palladium nitrate in the solution is converted to palladium oxide hydrate, the surface of the detector is not believed to have a contiguous palladium oxide hydrate coating. The surface of the detector seems to comprise palladium oxide hydrate concentrations in discrete zones or areas which are so small that the extreme magnification of an electron microscope is required to see them.

After the palladium nitrate is converted to palladium oxide hydrate, the resulting detector is desirably sensitized by heating the detector in an atmosphere containing from about 3 to about 9 volume percent of a combustible gas in air until the sensitivity is substantially increased, e.g., by 50%. Desirably at least 8 volume percent of combustible gas for ammonium chloropalladite is used and less than about 6 volume percent of combustible gas for palladium nitrate is used. Most preferably, from about 8 to about 8.8 volume percent of a combustible gas for ammonium chloropalladite solutions and 4.5 to 5.5 volume percent for palladium nitrate solutions are used. The heating temperature is from about 650° to about 825° C., preferably from about 725° C. to about 775° C., for from about 1 to about 30 minutes. The combustible gas is preferably methane. Heating at elevated temperatures, i.e., in excess of 775° C., in an air-gas mixture is to be avoided since the detector can readily burn out under those conditions. Furthermore, if the detector is heated much above 840° C., the oxide is lost and palladium metal remains. The oxide layer that builds back is thinner, tends to reduce the catalytic activity of the metal, and is itself less desirable catalytically than the oxide which was lost.

After sensitization, the detector is desirably stabilized by operating the sensor under controlled conditions so that the operating characteristics will be essentially constant in actual use. One such stabilization method is to operate the detector at 650° C. for one hour in air, for 18 hours in an atmosphere containing 2.5 volume percent methane, and again in air for 31 hours. The stabilization procedure is highly desirable when ammonium chloropalladite is used but may be shortened or eliminated when palladium nitrate is used.

It has been found in all steps requiring heating during the manufacture of the detector following curing of the binder, that a stepwise temperature rise is preferred over a gradual temperature change. The binder should be heated slowly to at least 255° C. to avoid foaming during dehydration.

In prior art detectors, the palladium catalyst is activated by reducing the oxide to the metal by high heat or by treatment with hydrazine. Next, the catalyst is aged in air or oxygen at a high temperature to reform the oxide. This procedure has been found to be highly undesirable since it results in a detector of lower sensitivity, shorter life, and lower calibration stability. The catalyst of this invention is activated by removing part, but not all, of the bound water and the water molecules believed to be trapped in the large palladium oxide hydrate molecule, which after partial removal is believed to increase the surface area of the catalyst particles. See O. Glemser and G. Peuschel, Z. inorg. Chem., 281, 44-53, 1955; or Chemical Abstracts, 50: 4612g, 1956. At no time in the processing is the original palladium oxide reduced all the way to the metal.

A marked difference between the detector of this invention and prior art detectors can be observed when detecting combustible gases in an atmosphere of pure nitrogen. The new detector maintains calibration for a long time of exposure to combustible gas, while prior art detectors lose calibration rather quickly.

The resulting element is utilized in a combustible gas sensing device which may comprise the element connected into a wheatstone bridge circuit which detects resistance changes in the element resulting from a temperature change in the device caused by a reaction of the device with a combustible gas. The circuit activates a warning means when a combustible gas is detected. The warning means may be any desirable warning device such as a light, buzzer, or other alarm, e.g., a mechanical vibrator. Usually the warning means is a warning light to be used in conjunction with an auditory signaling means.

In order to balance the wheatstone bridge circuit when such a circuit is used, a non-catalytic reference element is needed which has the same operating temperature resistance as the active element manufactured in accordance with this invention. The reference element is manufactured in the same way as the active element, except that it has no coating of palladium oxide. Such a standard reference element therefore permits the wheatstone bridge circuit to register resistance changes in the detecting element which are due solely to detection of a combustible gas by the element.

The reference element, which does not contain a palladium oxide coating, is instead coated with a compound which does not react with a combustible gas but which does react with changes in air temperature and changes in humidity of the surrounding air in a manner similar to the reaction of the active element with temperature and humidity in the surrounding air. A suitable coating for the reference element is potassium hydroxide. Alternatively, a thin layer of gold may be used as reference standard element surface coating.

Alternatively, an integrated circuit differential amplifier may be used to detect a change in detector resistance in place of the wheatstone bridge.

The element in accordance with the present invention is able to rapidly detect minute quantities of combustible gas in air. For example, such an element is capable of detecting carbon monoxide in concentrations of about 1 ppm and is able to detect hydrogen and methane in concentrations of less than 10 ppm.

Additionally, the operating temperature of the element in accordance with the invention can be as low as 250° C. and sometimes even as low as 50° C. when hydrogen is being detected, as low as 280° C. when carbon monoxide is being detected, and as low as from about 400° C. to about 600° C. when methane is being detected. Such low temperature operation substantially increases the useful life of the detection element as compared with prior art elements for detecting a combustible gas in air. Furthermore, the coating of the wire in accordance with the present invention substantially increases the durability of the element by reducing oxidation and vaporization of the wire. Operating at high temperatures, i.e., above 800° C., is to be avoided in order to prevent the palladium oxide coating from converting to metallic palladium as occurred in the prior art. Furthermore, the sensitivity of the novel detector remains more constant than the high temperature detectors of the prior art.

The size of the element manufactured in accordance with the invention is substantially smaller than known prior art elements for detecting a combustible gas. The reduced element size permits very small detection units to be manufactured which can be unobtrusively used. The low temperature operation and small size substantially reduces energy consumption of the element in accordance with the invention as compared with energy consumption required by prior art elements for detecting combustible gases in air, which permits the manufacture of portable instruments having a very small size and long battery life. The detector size may be from about 0.005 to about 0.25 cm in diameter and is preferably 0.02 to 0.1 cm in diameter. Some idea of the very small size of the detector can be appreciated when it is realized that the dot or period on a typewritten page would be within the above dimensions.

As seen in FIG. 1, the detector is connected to electrodes 26 by means of wire 12. The electrodes 26 in turn form a part of a detector assembly 28 which can be plugged into an electronic circuit.

It has been found that the small size of the detector has the added advantage of increasing the shock resistance of the assembly due to the smaller relative mass of the detector 10.

In addition, the detector in accordance with the invention is a very small sphere with greatly reduced associated convection energy, which can be placed in flame arrestor cavities having a much smaller inside radius about the detector than is possible with the much larger prior art detectors. The limit in size reduction is a radius or separation distance between the detector and the flame arrestor wall of approximately 0.14 cm. The practical result is a significantly reduced detector response time, which is particularly important in quickly detecting the heavier molecular weight toxic and combustible gases and vapors which diffuse more slowly.

The palladium oxide hydrate catalyst is believed to be a colloidal dispersion or sol with chemically bound and included water. It loses water when heated roughly in proportion to the temperature. It is believed that not all of the bound water is released even at temperatures as high as 800° C. A very small amount of water is bound in the hydrate so tenaciously that the decomposition temperature of the oxide must be reached before it can be released. In accordance with this invention, the processing of the detector is carried out so that the decomposition temperature of the hydrate or oxide is never reached. When most of the water is removed, the structure is believed to have a substantially increased surface area similar to dehydrated or activated aluminum catalyst carriers. See J. R. Anderson, Structure of Metallic Catalysts, page 168, Academic Press, 1975. Dehydrated palladium hydroxide, palladium oxide, and palladium metal from reduced palladium chloride are not believed to have a similarly increased surface area.

To get the large palladium oxide hydrate molecule described by Glemser, the starting solution should be weakly acid. To achieve optimum catalyst dispersion in a reasonable number of coats, a concentration of palladium nitrate is required which results in a very acid solution having a pH at about 0.57 due to hydrolysis. If one attempts to bring the solution to a suitably higher pH value by titrating with $NH_4OH$, insoluble palladium hydroxide is precipitated. Nitrate ions are therefore preferably removed, to produce a weakly acid solution, by extraction with a water insoluble, high molecular weight organic amine. See Yu. G. Frolov et al, Theoretical Aspects of Amine Extraction, Atomic Energy Review, 7 (1), 71–138, 1969. For use in this invention, the amine should be a liquid insoluble in water, have a boiling point above that of water, contain no chlorine or other catalyst poisons, have a density substantially different than water to facilitate separation, and be characterized by low toxicity. Tertiary octyl amine has been found to be particularly desirable. In the preferred embodiment, a sufficient amount of tertiary octyl amine is shaken with the catalyst solution to produce a hydrolyzed palladium nitrate solution with a pH between 2.5 and 4.5.

In all cases herein, where a hydrolyzed nitrate is converted to an oxide hydrate or oxide at a temperature of between about 100° C. and 750° C., the conversion takes place in an oxygen containing atmosphere such as air and the conversion time is from about 10 seconds to about 15 minutes.

An instrument utilizing the detector disclosed herein is not position sensitive, that is, the instrument reading, either in air or when detecting a combustible gas, does not go off calibration due to changes in the instrument position. It is believed that the position stability of the detector is due to its small size and spherical shape. Prior art detectors frequently had oval, cylindrical or flat shapes which are believed to contribute to their position sensitivity. To obtain meaningful instrument readings, it has been found that reference elements should be of the same shape and size as the detector.

EXAMPLE I

A precision winding machine is used to wind thirteen turns of resistance grade platinum wire having a diameter of 0.00127 cm about a clean and deoxidized molybdenum wire to form a coil. The molybdenum wire has a diameter of 0.0434 cm and the spacing between turns is maintained at about 0.00127 cm.

Five percent aluminum oxide ($Al_2O_3$), which is completely sintered alpha alumina ground to a particle size of 0.5 micron or smaller, is then blended into a solution containing chromic and phosphoric acids to form a ceramic precursor having a dry molar ration of about $Al_2O_3:0.8Cr_2O_3:3P_2O_5$. The resulting blend is then coated over the coil as a binding cement. The mandrel containing the coated coil is then heated to about 250° C. by passing an electric current through the mandrel to dry the cement. The mandrel is then further heated to about 530° C. to cure the binder.

The mandrel is then removed by dissolving it in an acid solution containing 30% of 65% nitric acid solution, 30% of 98% sulfuric acid solution and 40% distilled water.

The coil is then washed in distilled water and dried. The ends of the coils are then welded to nickel supports or posts which are mounted to a base on 0.381 cm centers.

Solutions are prepared for further treating the coil. Each of the solutions is thoroughly mixed at room temperature and allowed to stand overnight before use. High purity chemicals and distilled water are used.

The prepared solutions are as follows:

| | |
|---|---|
| Aluminum nitrate solution: | |
| $Al(NO_3)_3 \cdot 9H_2O$ | 44 weight percent |
| $H_2O$ | 56 weight percent |
| Thorium nitrate solution: | |
| $Th(NO_3)_4 \cdot 4H_2O$ | 62 weight percent |
| $H_2O$ | 38 weight percent |
| Catalyst solution: | |
| $Pd(NO_3)_2$ | 5.9 weight percent |
| $H_2O$ | 94.1 weight percent |

The catalyst solution is shaken with tertiary octyl amine for less than ten minutes in a small separator funnel and then allowed to stand to bring the pH to about 3. The amine rises to the top, or it is separated in a centrifuge, and the amine and any particulate residue is discarded. Care must be taken that the palladium nitrate solution is kept near room temperature, since $PdO \cdot nH_2O$ will precipitate at higher water temperatures.

The coil is heated by passing an electric current through it, i.e., ohmically, to a temperature of 600° C. for 25 seconds, which is believed to remove any residual moisture or organic compounds, and such heating is repeated when the coil has been allowed to stand for over 15 minutes at any time during the processing.

The coil is then wetted with the foregoing solutions in the order specified in Table I to the temperature and for the times specified in Table I.

TABLE I

| Number of Coats | Solution | Temperature Degrees C. | Duration Sec. |
|---|---|---|---|
| 1 | Aluminum nitrate | 250 | 10 |
| | | 350 | 10 |
| 1 | Aluminum nitrate | 250 | 10 |
| | | 350 | 10 |
| | | 500 | 10 |
| 2 | Aluminum nitrate | 350 | 10 |
| | | 500 | 10 |
| 2 | Thorium nitrate | 250 | 10 |
| | | 350 | 10 |
| | | 500 | 10 |
| 15 | Palladium catalyst solution | 350 | 10 |
| | | 500 | 10 |

After coating is completed, the resulting coated coil, i.e., detector, is activated to maximize and to stabilize the detector performance. The activation is carried out in a metal chamber equipped with automatic controls which switch from one supply gas to another. The chamber has an internal volume of about 1 cubic centimeter. The detector is initially exposed to air flow of 1 liter per minute at room temperature followed by a combustible gas-air mixture at about 0.1 liter per minute for 15 seconds. The detector is then electrically, i.e., ohmically, heated to 750° C. for about fifteen minutes. The electric current is then turned off and the detector is allowed to cool for about 10 seconds. The combustible gas flow is then turned off and the air flow is again turned on. After 10 more seconds, the activated detector is removed from the chamber. The air-gas mixture which is used comprises about 5.5 percent by volume methane, i.e., $CH_4$, in air.

The detector is then aged by electrically heating the detector to 650° C. for 1 hour at 0.3 liters per minute of dry air, followed by 16 hours at 0.3 liter per minute of air containing about 2.5 percent methane, followed by 31 hours in air at 0.3 liters per minute. When heated to 650° C., the resulting detector shows a 9 to 12% change in resistance when exposed to 2.5 volume percent methane in air. In addition, the detector expends only 150 milliwatts of energy during operation and has a volume of only 0.00018 cubic centimeters.

The discussion herein is primarily directed to extremely small detectors which respond to oxidation reactions of combustible gases and their method of manufacture; however, the disclosure herein with respect to small coils, is applicable to any detector utilizing a coil and operating at an elevated temperature such as semiconductor gas detectors and solid electrolyte gas detectors.

What is claimed is:

1. An element which, at a temperature of below about 600° C., undergoes a change in electrical resistance when exposed to a combustible gas in air, said element comprising a wire coated with a solution of a palladium compound which is heated to from about 100° C. to about 600° C. to form a palladium oxide composition.

2. The element of claim 1 wherein the wire comprises a metal or metal alloy having a melting temperature above 1,500° C., the solution is a palladium nitrate solution, and the palladium oxide composition is palladium oxide hydrate.

3. The element of claim 2 wherein the wire has a circular cross section, has a diameter of from about 0.0001 cm to about 0.0025 cm, and is in the form of a coil having a coil diameter of from about 0.01 to about 0.1 cm.

4. The element of claim 3 wherein the metal or metal alloy is platinum or a platinum alloy.

5. The element of claim 4 wherein the metal is platinum.

6. The element of claim 4 wherein the metal is an alloy of platinum and about ten weight percent rhodium.

7. The element of claim 3 wherein a coating comprising amorphous water-insoluble cured ceramic binder is present between the wire and the palladium oxide composition.

8. The element of claim 7 wherein the cured ceramic binder comprises a cured ceramic precursor solution comprising phosphoric acid and aluminum oxide wherein the molar ratio of phosphoric acid to aluminum oxide is from about 3:1 to about 3.5:1.

9. The element of claim 4 wherein a coating of ceramic material is present between the wire and the palladium oxide composition.

10. The element of claim 9 wherein said solution contains chromic acid in a molar ratio to phosphoric acid of about 0.8:3.

11. The element of claim 2 wherein a coating of thorium oxide is present between the cured ceramic coating and the palladium oxide composition.

12. The element of claim 10 wherein the ceramic coating is between 0.001 cm and about 0.025 cm thick.

13. The element of claim 12 wherein a thorium oxide coating between about 0.001 cm and about 0.025 cm thick is present between the aluminum oxide and the palladium oxide composition.

14. The element of claim 1 wherein the wire has a circular cross section, has a diameter of from about 0.0001 cm to about 0.0025 cm, and is in the form of a coil having a coil diameter of from about 0.01 to about 0.1 cm.

15. A method for manufacturing an element which at a temperature of below about 600° C. undergoes a change in resistance when exposed to a combustible gas in air which method comprises:
(a) winding a wire, having a diameter of from about 0.0001 cm to about 0.005 cm, comprising a metal or metal alloy having a melting temperature above 1500° C., around a mandrel having a diameter of from about 0.01 to about 0.1 cm to form a wire coil, said mandrel being more susceptible to oxidation than the wire;
(b) coating the coil with a ceramic precursor;
(c) heating said coated coil to above about 250° C. to dehydrate and cure said coating;
(d) removing said mandrel by chemical or thermal oxidation;
(e) coating said coil with a palladium containing solution which comprises from about 1 to about 50 weight percent of palladium compound which will form a palladium oxide composition upon sufficient heating to from about 250° C. to about 750° C.; and
(f) heating said coil to a temperature of from about 250° C. to about 750° C. for from about 1 to about 60 seconds to convert the palladium compound to a palladium oxide composition.

16. The method of claim 15 wherein the ceramic precursor comprises from about 20 to about 50 percent by total weight of solution of aluminum oxide and phosphoric acid said aluminum oxide having a molar ratio to phosphoric acid of from about 1:3 to about 1:3.5, said aluminum oxide having a particle size of less than about 0.5 micron.

17. The method of claim 15 wherein the palladium containing solution is a palladium nitrate solution which is adjusted to a pH of from about 2 to about 4 with an amine and the palladium oxide composition is palladium oxide hydrate.

18. The method of claim 17 wherein prior to coating said coil with a solution of palladium nitrate, said coil is coated with a solution containing from about 5 to about 60 weight percent of aluminum nitrate and heated to between about 250° C. and about 750° C. to convert said aluminum nitrate to aluminum oxide.

19. The method of claim 14 wherein subsequent to coating with aluminum nitrate solution and prior to coating with palladium nitrate solution, said coil is coated with a solution containing from about 5 to about 70 weight percent of thorium nitrate and heated to between about 250° C. and about 750° C., to convert said thorium nitrate to thorium oxide.

20. The method of claim 19 wherein up to about ten repeated applications and conversions of aluminum nitrate solution are made prior to application of a thorium nitrate or a palladium nitrate solution.

21. The method of claim 20 wherein up to about ten repeated applications and conversions of thorium nitrate solution are made after applications and conversions of aluminum nitrate and before application of palladium nitrate.

22. The method of claim 17 wherein up to about 20 applications and conversions of palladium nitrate solution are made.

23. The method of claim 21 wherein up to about 20 applications and conversions of palladium nitrate solution are made.

24. The method of claim 17 wherein said wire comprises platinum or a platinum alloy.

25. The method of claim 24 wherein said mandrel comprises a molybdenum cylinder.

26. The method of claim 25 wherein said mandrel is removed by dissolving it in an aqueous solution containing from about 15 to about 40 parts by weight sulfuric acid; from about 15 to about 40 parts by weight nitric acid and from about 30 to about 70 parts by weight water.

27. The method of claim 25 wherein said mandrel is removed by heating in air at a temperature of between about 750° C. and about 1000° C.

28. The method of claim 17 wherein the palladium nitrate solution is prepared by reacting palladium chloropalladite with nitric acid.

29. The method of claim 17 wherein a solution containing from about 4 to about 7 weight percent palladium nitrate is used.

30. The method of claim 18 wherein subsequent to heating said coated coil to from about 250° C. to about 750° C., to convert palladium nitrate to palladium oxide, said coated coil is activated by heating the coil to between about 650° C. and 825° C. in an atmosphere containing from about 3 to about 9 volume percent of a combustible gas in air until the sensitivity is substantially increased.

31. The method of claim 30 wherein an aluminum nitrate solution containing from about 35 to about 55 weight percent aluminum nitrate is used.

32. The method of claim 30 wherein said coated coil is activated by heating the coil between about 725° and about 775° C. for from about 1 to about 30 minutes and said atmosphere contains a combustible gas concentration from about 3 to about 6 volume percent of methane.

33. A combustible gas sensing device comprising the element of claim 1 connected into a wheatstone bridge circuit which detects resistance changes in the element resulting from a temperature change in the element caused by reaction of the element with a combustible gas and which circuit upon such detection activates a warning means.

34. A combustible gas sensing device comprising the element of claim 2 connected into a wheatstone bridge circuit which detects resistance changes in the element resulting from a temperature change in the element caused by reaction of the element with a combustible gas and which circuit upon such detection activates a warning means.

35. A combustible gas sensing device comprising the element of claim 3 connected into a wheatstone bridge circuit which detects resistance changes in the element resulting from a temperature change in the element caused by reaction of the element with a combustible gas and which circuit upon such detection activates a warning means.

36. A combustible gas sensing device comprising the element of claim 4 connected into a wheatstone bridge circuit which detects resistance changes in the element resulting from a temperature change in the element caused by reaction of the element with a combustible gas and which circuit upon such detection activates a warning means.

37. A combustible gas sensing device comprising the element of claim 7 connected into a wheatstone bridge circuit which detects resistance changes in the element resulting from a temperature change in the element caused by reaction of the element with a combustible gas and which circuit upon such detection activates a warning means.

38. A combustible gas sensing device comprising the element of claim 8 connected into a wheatstone bridge circuit which detects resistance changes in the element resulting from a temperature change in the element caused by reaction of the element with a combustible gas and which circuit upon such detection activates a warning means.

39. A combustible gas sensing device comprising the element of claim 10 connected into a wheatstone bridge circuit which detects resistance changes in the element resulting from a temperature change in the element caused by reaction of the element with a combustible gas and which circuit upon such detection activates a warning means.

40. A combustible gas sensing device comprising the element of claim 13 connected into a wheatstone bridge circuit which detects resistance changes in the element resulting from a temperature change in the element caused by reaction of the element with a combustible gas and which circuit upon such detection activates a warning means.

41. The device of claim 27 wherein the warning means comprises a warning light.

42. The device of claim 33 wherein the warning means comprises a warning light.

43. The device of claim 36 wherein the warning means comprises a warning light.

44. The method of claim 32 wherein said wire is platinum or palladium, said mandrel is molybdenum, and said precursor comprises aluminum phosphate, phosphoric acid, chromium phosphate, submicron aluminum oxide, and water.

45. The element of claim 1 wherein the palladium compound is palladium nitrate or ammonium chloropalladite.

46. The method of claim 15 wherein the palladium compound is palladium nitrate or ammonium chloropalladite.

* * * * *